(12) United States Patent
Horvath

(10) Patent No.: US 8,308,716 B2
(45) Date of Patent: Nov. 13, 2012

(54) APPARATUS AND METHOD FOR AUTO-TITRATING A LASER

(75) Inventor: Christopher Horvath, Irvine, CA (US)

(73) Assignee: Novartis AG, Basel (CH)

( * ) Notice: Subject to any disclaimer, the term of this patent is extended or adjusted under 35 U.S.C. 154(b) by 1470 days.

(21) Appl. No.: 11/768,576

(22) Filed: Jun. 26, 2007

(65) Prior Publication Data

US 2008/0004609 A1 Jan. 3, 2008

Related U.S. Application Data

(60) Provisional application No. 60/818,002, filed on Jun. 30, 2006.

(51) Int. Cl.
*A61B 18/18* (2006.01)
(52) U.S. Cl. ............ 606/4; 606/5; 606/10; 607/89
(58) Field of Classification Search ............ 606/2–19; 607/88–93
See application file for complete search history.

(56) References Cited

U.S. PATENT DOCUMENTS

| | | | |
|---|---|---|---|
| 3,747,019 A | | 7/1973 | Koechner et al. |
| 4,895,154 A | * | 1/1990 | Bartelt et al. ............ 607/50 |
| 5,260,953 A | | 11/1993 | Rowe |
| 5,993,441 A | * | 11/1999 | Muller et al. ............ 606/10 |
| 6,090,102 A | | 7/2000 | Telfair et al. |
| 6,129,723 A | | 10/2000 | Anderson et al. |
| 6,595,985 B1 | * | 7/2003 | Tobinick ............ 606/9 |
| 2001/0010003 A1 | | 7/2001 | Lai |
| 2002/0099363 A1 | * | 7/2002 | Woodward et al. ............ 606/5 |
| 2002/0125228 A1 | | 9/2002 | Smart et al. |

(Continued)

FOREIGN PATENT DOCUMENTS

WO WO 01/26591 4/2001

(Continued)

OTHER PUBLICATIONS

Carl D. Regillo, Gary C. Brown, Harry W. Flynn. Vitreoretinal disease: the essentials. 1998.*

(Continued)

*Primary Examiner* — Henry M Johnson, III
*Assistant Examiner* — Lynsey Crandall
(74) *Attorney, Agent, or Firm* — Darien Reddick

(57) ABSTRACT

An apparatus and method for auto-titrating a surgical laser are disclosed. One embodiment of the method comprises: providing an algorithm, wherein the algorithm is operable to configure the laser based on one or more user inputs; providing a first user input operable to cause the algorithm to execute and fire the laser in a defined pattern; providing a second user input, in response to an observed condition, operable to cause the laser to stop firing and to cause the algorithm to determine one or more laser parameter values and configure the laser based on the one or more laser parameter values, wherein a final laser power value when the laser stops firing is an input to the algorithm and wherein the algorithm determines the one or more laser parameters based on the final laser power value. The method can further comprise placing the laser in a "ready" (surgical) mode, either automatically by the auto-titration algorithm or via another user input. Once in a ready mode, a user, such as a surgeon, can perform a surgical procedure with the automatically configured laser. The user inputs can be provided by activating a control switch, such as the footswitch typically used by ophthalmic surgeons to control the operation of an ophthalmic surgical laser.

29 Claims, 3 Drawing Sheets

U.S. PATENT DOCUMENTS

| | | | |
|---|---|---|---|
| 2004/0098070 A1* | 5/2004 | Mohr et al. | 607/89 |
| 2006/0020309 A1* | 1/2006 | Altshuler et al. | 607/88 |
| 2006/0084954 A1* | 4/2006 | Zadoyan et al. | 606/11 |
| 2006/0111697 A1* | 5/2006 | Brinkmann et al. | 606/4 |
| 2006/0139722 A1* | 6/2006 | Kayser et al. | 359/246 |
| 2008/0167642 A1* | 7/2008 | Palanker et al. | 606/4 |

FOREIGN PATENT DOCUMENTS

| | | |
|---|---|---|
| WO | WO 01/91458 | 11/2001 |
| WO | WO 02/076119 | 9/2002 |
| WO | WO 02/076319 | 10/2002 |
| WO | WO 2005/007002 | 1/2005 |

OTHER PUBLICATIONS

Thomas R. Frieberg, M.D., et al., The Treatment of Macular Disease Using a Micropulsed and Continuous Wave 810-nm Diode Laser, Ophthalmology, Dec. 1997, vol. 104, No. 12.

International Search Report for PCT/US2006/038086, Publication No. W02007/041304, 4 pages.

European Search Report for Application No. 07111216.3, Publication No. 1872754, Published Jan. 2, 2008, 3 pages.

* cited by examiner

APPARATUS AND METHOD FOR AUTO-TITRATING A LASER

CROSS-REFERENCE TO RELATED APPLICATIONS

This application claims priority under 35 U.S.C. §119 to U.S. Provisional Patent Application No. 60/818,002, filed Jun. 30, 2006, the entire contents of which are incorporated herein by reference.

TECHNICAL FIELD OF THE INVENTION

The present invention relates in general to laser systems. In particular, the present invention relates to surgical laser systems. Even more particularly, the present invention relates to a system and method for automatic titration of a laser for use in ophthalmic surgery.

BACKGROUND OF THE INVENTION

A number of ophthalmic surgical procedures performed on a patient's eye, such as on the retina, require irradiating a select portion of the eye with a light spot, typically provided by a laser, having a desired spot size. Examples of surgical procedures utilizing lasers include photo-dynamic therapy, LASIK, laser sclerlostomy, trabeculectomy, and general endoscopic microsurgical applications, including neural, arthroscopic, and spinal chord surgery.

In one particular ophthalmic surgical procedure, typically referred to as retinal coagulation, a laser light spot is directed to a selected portion of a patient's retina to deposit energy, thereby causing coagulation of the local tissue. Such a photocoagulation procedure can be employed, for example, to seal leaky blood vessels, destroy abnormal blood vessels, or seal retinal tears. In preparation for such a laser procedure, and others, a surgeon typically must place several probing laser shots onto the retina to titrate the laser power for an intended surgical effect. The surgeon will typically start out with the laser set to a low power setting and incrementally increase the laser power until he or she observes a desired tissue effect (e.g., discoloration) indicating that the laser power is at or beyond a level required for the intended procedure. The surgeon will then finalize the laser power setting and treat the intended area.

The laser titrating procedure is performed manually by the surgeon, as currently existing surgical lasers and surgical laser systems do not provide the ability to auto-titrate a surgical laser. If aspects of the laser titration procedure were instead automated, a surgeon could be freed from the additional setup steps required to set the surgical laser power for a surgical procedure, thus improving the efficiency and flow of the surgical procedure.

Therefore, a need exists for an apparatus and method for automatically titrating a surgical laser that can reduce or eliminate the problems of prior art surgical lasers associated with manually titrating the surgical laser in preparation for a surgical procedure.

BRIEF SUMMARY OF THE INVENTION

The embodiments of the auto-titrating laser apparatus and method of using a surgical laser of the present invention substantially meet these needs and others. One embodiment of the method for auto-titrating a laser comprises: providing an algorithm, wherein the algorithm is operable to configure the laser based on one or more user inputs; providing a first user input operable to cause the algorithm to execute and fire the laser in a defined pattern; providing a second user input, in response to an observed condition, operable to cause the laser to stop firing and to cause the algorithm to determine one or more laser parameter values and configure the laser based on the one or more laser parameter values, wherein a final laser power value when the laser stops firing is an input to the algorithm and wherein the algorithm determines the one or more laser parameters based on the final laser power value. The method can further comprise transitioning (placing) the laser to a "ready" (surgical) mode, either automatically by the auto-titration algorithm or via another user input. Once in a ready mode, a user, such as a surgeon, can perform a surgical procedure with the automatically configured laser. The surgeon can thus transition quickly and efficiently to performing the intended surgery with the laser automatically configured to his or her pre-defined settings.

One benefit of the embodiments of the present invention over the prior art is thus the ability to automate portions of a titration procedure and settings and thereby improve the flow and efficiency of a surgical procedure. A surgeon can, for example, select a pre-defined titration ramp and initiate a pre-defined laser pulse sequence by activating a control switch, such as the footswitch typically used by ophthalmic surgeons to control the operation of an ophthalmic surgical laser. The surgeon can release the footswitch (or other control apparatus) upon observing a desired effect on the tissue being irradiated by the laser's beam. The time indication (interval) of the control device release can be used by the surgical laser system to configure certain laser operating parameters, such as laser power and pulse duration, for an intended surgical procedure based on the surgeon's pre-defined criteria. The operating parameters set by the embodiments of the present invention may be higher, lower or correspond to the settings at the time of the control apparatus' release depending on the surgeon's predefined criteria.

Embodiments of the present invention can comprise an apparatus for auto-titrating a surgical laser, comprising a processing module and a memory operably coupled to the processing module, wherein the memory includes computer-executable software instructions operable to cause the processing module to perform at least some of the functions described herein. Embodiments of the apparatus for auto-titrating a surgical laser can further comprise hardware operable to perform at least some of the functions described herein in response to signals from the processing module.

Embodiments of the present invention can be implemented within any ophthalmic surgical laser system as known to those having skill in the art, and in particular, in the EYELITE® Laser Surgical System manufactured by Alcon Manufacturing, Ltd. of Irvine, Calif. The embodiments of this invention can be incorporated within any such surgical machine or system for use in ophthalmic or other surgery. Other uses for an apparatus and method for auto-titrating a laser in accordance with the teachings of this invention will be known to those having ordinary skill in the art and are contemplated to be within the scope of this invention.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings in which like reference numerals indicate like features and wherein.

DETAILED DESCRIPTION OF THE INVENTION

Figure 1:
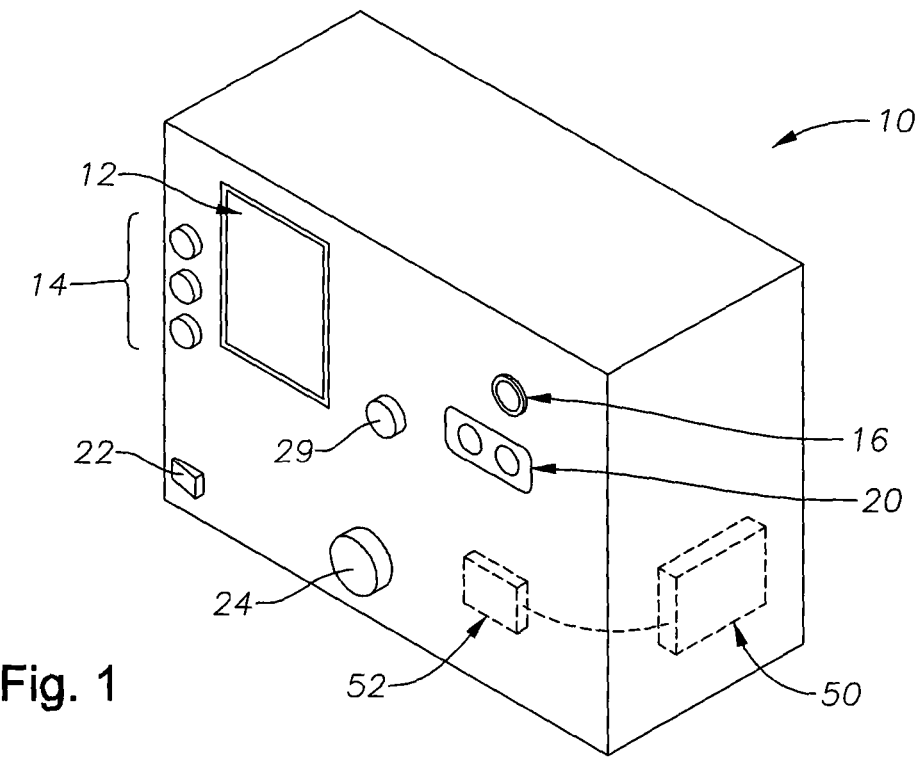
FIG. 1 is a diagrammatic representation of an exemplary surgical laser console in which an embodiment of the apparatus and method for auto-titrating a laser of the present invention can be implemented.

Preferred embodiments of the present invention are illustrated in the FIGURES like numerals being used to refer to like and corresponding parts of the various drawings.

The various embodiments of the present invention provide an auto-titrating surgical laser and an apparatus and method of auto-titrating a laser, such as a surgical laser, that provide a user, such as a surgeon, the ability to automatically configure certain laser parameters, in particular laser power, for use in a surgical procedure based on an observed effect and a pre-defined configuration (titration) routine. Embodiments of the present invention can comprise an auto-titrating surgical laser, an apparatus for auto-titrating a laser, and a method for configuring a laser.

The embodiments of the present invention provide a surgeon the ability to automate a prior-art manual titration process in which a surgeon fires test shots to create test "burns" on the periphery of the retina, where burning causes negligible effects on a patient's vision, at various incrementally increasing laser power settings until a desired effect, such as whitening of the affected section of the retina, is observed. Once the whitening effect is observed, the surgeon knows that the laser power is higher than desired for retinal surgery, and he or she can set the laser power to a lower setting appropriate for an intended surgical result that will not cause unintended effects to the patient's retina (e.g., damage). For example, the surgeon can choose to lower power by a given factor (e.g., 20%). Typically, whitening of the retina at the test site indicates a laser power setting higher than desired for the surgical procedure.

Prior art surgical laser systems require a surgeon to manually titrate the surgical laser, adjusting power in increments and then manually setting the power to a desired operational value once the tissue effect is observed. The embodiments of the present invention automate aspects of the titration procedure such that a surgeon can instead pre-define a titration algorithm that can automatically configure a surgical laser's parameters at the initiation of the surgeon. For example, one embodiment of this invention provides for an auto-titration function that allows the surgeon to pre-define one or more of pulse rate, pulse duration, laser power increments, initial power and maximum laser power. The surgeon can also pre-define the laser's surgical (operational) power setting (i.e., the laser power used during the surgical procedure), for example, as a function of the final titration power setting (the power setting at the point the desired tissue effect is observed and the surgeon stops the test shots). For example, the surgical power setting might be set 20% less than the final titration power setting. Other parameter settings, as will be known to those having ordinary skill in the art, can also be pre-defined for automatic configuration by an embodiment of the auto-titration algorithm of this invention.

Once the surgeon has pre-defined the auto-titration function, the embodiments of the present invention operate to execute the function and automatically configure the surgical laser parameters for a surgery based on an input from the surgeon. The input could be the surgeon, while preparing for surgery, actuating a control interface, such as a button, a screen icon, a footswitch, or any other control mechanism operable to activate the laser or a laser function. In one embodiment, for example, the surgeon can actuate a footswitch to fire the laser. In accordance with the embodiments of this invention, the surgeon can activate the footswitch and fire the laser while in the titration mode (which can be initiated via a control interface on the surgical laser/console), thus running the preset titration program (e.g., power increments, pulse durations, etc.) and placing one or more test shots on the patient's retina. Once the surgeon observes a desired tissue effect indicating a desired laser power setting, he or she can deactivate the laser (e.g., release the footswitch), which will cause the auto-titration program to automatically configure the selected laser parameters, in particular laser power, to the selected surgical settings in accordance with the pre-defined criteria of the auto-titration program. The time indication (duration the surgeon fires laser test shots) is a primary input to determine surgical laser settings based on the laser operating parameters at the time the surgeon stops the laser test firing (titration). Once the auto-titration program sets the laser parameters to their surgical values, the surgical laser can be automatically transitioned into treatment mode and the surgeon can carry out the surgical procedure without interruption.

FIG. 1 is a diagrammatic representation of an exemplary surgical laser console in which an embodiment of the apparatus and method for auto-titrating a laser of the present invention can be implemented. Laser 10 includes a user interface 12, various control knobs and/or buttons 14, probe port 16, illumination port 20, on/off key 22, and emergency shut-off 24. These control devices are exemplary only and a surgical laser/laser console may have any combination of these and perhaps other control interfaces and ports that may be useful in an ophthalmic laser system. User interface 12 can be a graphical user interface, including a touch-sensitive screen, as will be known to those having ordinary skill in the art, for displaying and allowing a user to select functions and control/adjust parameters of the laser system 10. The various other controls and ports shown in FIG. 1 can serve functions that will be apparent to those having ordinary skill in the art of ophthalmic laser systems.

Laser 10 can further include a processing module 50 and an associated memory 52, operably coupled to one another and to the control functions of the surgical laser 10 console. The processing module 50 and the memory 52 are operable to store and execute operational instructions operable to cause laser 10 to fire, change settings, and other functions associated with a laser 10 as will be familiar to those of ordinary skill in the art. Processing module 50 and memory 52, in particular, are operable to store and execute computer (processing module) executable software/operational instructions operable to cause laser to perform at least some of the functions of the method/algorithm of this invention described herein. Such instructions can be hard-code and or operational instructions stored in memory 52 and corresponding to at least some of the steps or functions described herein.

Processing module 50 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. Memory 52 may be a single memory device, a plurality of memory devices, and/or embedded circuitry of the processing module. Memory 52 may be a read-only memory, random access memory, volatile memory, non-volatile memory, static memory, dynamic memory, flash memory, cache memory, and/or any device that stores digital information. Note that when the processing module 50 implements one or more of its functions via a state machine, analog circuitry, digital circuitry, and/or logic circuitry, the memory 52 and/or memory element storing the corresponding operational instructions may be embedded within, or external to, the circuitry comprising the state machine, analog circuitry, digital circuitry, and/or logic circuitry. Further note that, the memory element stores, and the processing module executes, hard coded and/or operational instructions corresponding to at least some of the steps and/or functions illustrated in FIGS. 1-4.

As one of ordinary skill in the art will appreciate, user interface 12 corresponds generally to any user interface within an ophthalmic surgical system that employs a surgical laser. In particular, user interface 12 can be used by a user, such as a surgeon, to enter/program an embodiment of the pre-defined auto-titration procedure of the present invention. For example, the user can input via a graphical user interface 12 and the other control devices of laser 10 the laser starting power, pulse duration, inter-pulse time, power step increments, maximum allowed laser power, surgical power setting offset from final titration power setting (e.g., at footswitch release), single/multi shot pattern, etc.

Figure 2:
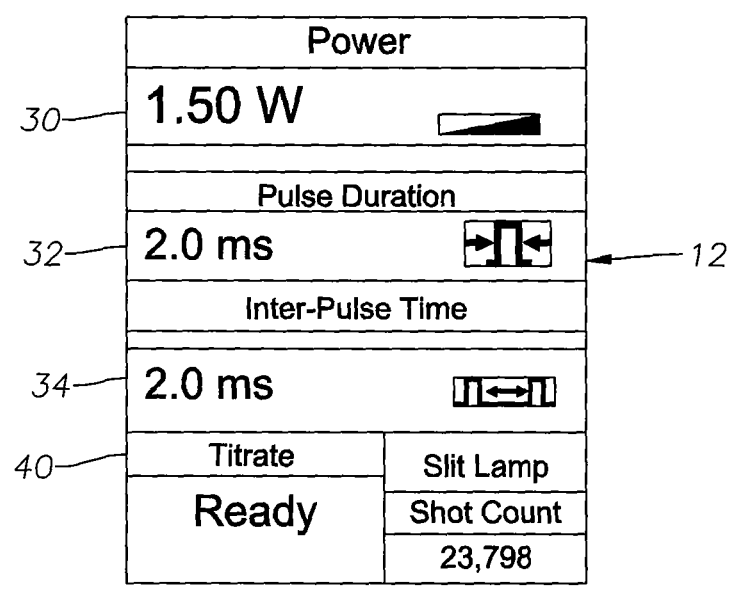
FIG. 2 is a close-up view of one embodiment of a user interface 12 in accordance with the present invention.

FIG. 2 is a close-up view of one embodiment of a user interface 12 in accordance with the present invention. At user interface 12, a user can, for example, adjust the laser power 30, pulse duration 32 or inter-pulse time 34 by touching the screen at the respective function label. The user interface 12 can then, for example, bring up a graphical slider (not shown) that the user can use to adjust the parameter by sliding his/her finger across the screen in a manner that will be well known to those having ordinary skill in the art. The surgeon can thus pre-define a titration procedure with the functions shown in FIG. 2 as well as others (e.g., maximum laser power, surgical power offset percentage, etc.). A current, or previously stored titration program can then be selected via user interface 12 and activated by the surgeon by, for example, activating a laser firing footswitch or other device. A titration program can be selected and made ready for activation by the surgeon by placing the laser 10 in a titration mode, which can be done, for example, by selecting such a mode at the user interface 12, for example, by selecting titrate button 40, or by actuating a dedicated titration-mode switch 29 of FIG. 1, a soft switch, or by any other such control on the surgical laser 10.

Figure 3:
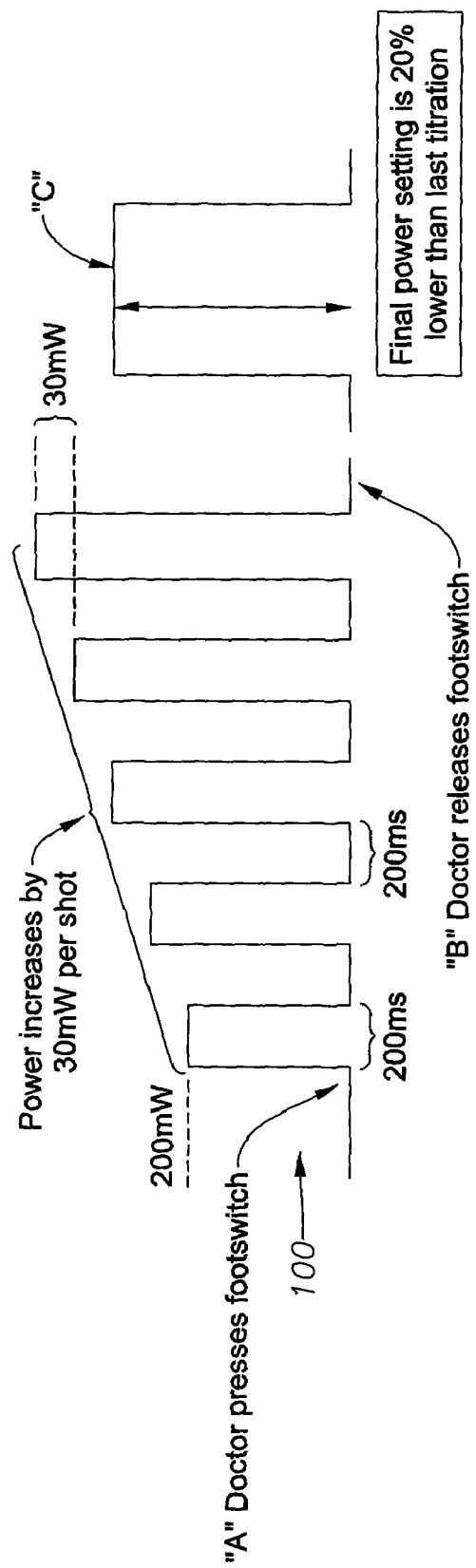
FIG. 3 is a graphical representation of the power vs. time profile of one predefined titration procedure in accordance with an embodiment of this invention.

FIG. 3 is a graphical representation of the power vs. time profile of one predefined titration program/algorithm in accordance with an embodiment of this invention. In the example of graph 100, the surgeon selects, for example, a starting laser power of 200 mW, a pulse duration of 200 ms, an inter-pulse time of 200 ms, a power step increment of 30 mW, a maximum allowed power of 500 mW and a surgical laser power setting offset from final titration power of −20% (i.e., once the surgeon stops the laser test shots upon observing a desired tissue effect by, for example, releasing a footswitch or other actuator, the titration procedure will automatically set the surgical laser power at 20% less than the laser power upon footswitch release). The surgeon can program these titration settings at the laser 10 via the user interface 12 and can, if desired, save the titration settings for later recall.

As previously discussed, a surgeon can initiate the auto-titration mode by, for example, depressing a footswitch, or a button, or virtual button, on a laser 10 console. As shown in FIG. 3, at point A, the surgeon presses the actuation mechanism (e.g., a footswitch) to fire laser 10 and the automatic titration sequence/algorithm is initiated and controls the firing of the laser 10 in accordance with the auto-titration algorithm/program. From point A to point B the laser power increases in 30 mW increments every 200 ms and each pulse has a 200 ms duration. At point B, the surgeon releases the actuator and the laser firing stops. The final, surgical power setting is automatically set to 20% less than the power at point B (as shown at point C) by the titration algorithm of this invention. Once the power has been adjusted to its surgical value, the laser 10 can be automatically transitioned to a "surgical mode" (i.e., the auto-titration mode is terminated and the laser is "ready") without further input from the surgeon and the laser 10 is ready for surgery. The surgeon can thus transition quickly and efficiently to performing the intended surgery with laser 10 automatically configured to his or her pre-defined power setting and any other pre-defined parameter settings. If the surgeon decides that the auto-configured surgical power setting is inappropriate for the surgery, he or she can repeat the procedure above or adjust the power manually.

Figure 4:
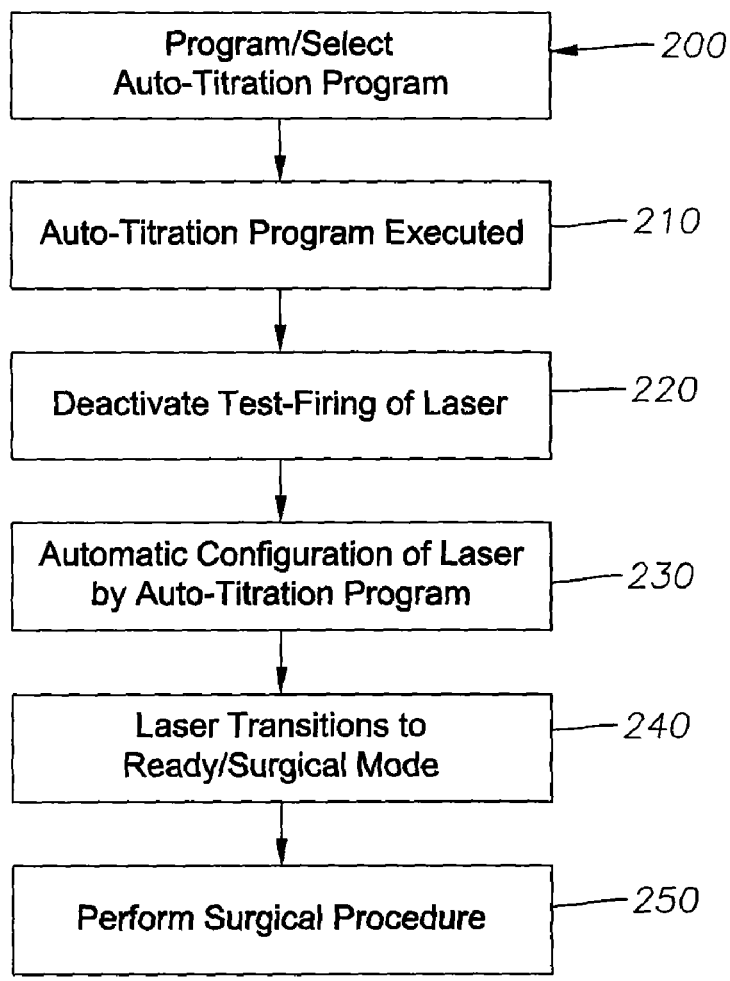
FIG. 4 is a flowchart illustrating the steps of one embodiment of the method of this invention.

FIG. 4 is a flowchart illustrating the steps of one embodiment of the method of this invention. At step 200 a user programs and/or selects an auto-titration program in a manner as described above. Step 200 can also comprise the user placing the surgical laser 10 into a titration-mode as previously described. At step 210, the user executes the selected auto-titration program by, for example, pressing an actuation mechanism, such as a footswitch, to fire laser 10 (one or more test shots to titrate laser 10). The automatic titration sequence is initiated and controls the firing of the laser 10 in accordance with the selected titration program. At step 220, upon observing a desired tissue response at the test shot locations, the user stops the firing of laser 10 by, for example, releasing the actuation mechanism. At step 230, in response to the surgeon's input (deactivating laser), the auto-titration program automatically configures selected laser parameters corresponding to the selected auto-titration program in accordance with the pre-defined criteria of the auto-titration program. At step 240, the laser 10 is transitioned to a "ready" (surgical) mode, either automatically by the auto-titration program or via another user input, and, at step 250, the surgeon can perform the surgical procedure. The surgeon can thus transition quickly and efficiently to performing the intended surgery with laser 10 automatically configured to his or her pre-defined power setting and any other pre-defined parameter settings. Embodiments of the method of this invention can comprise some or all of the steps described above.

Figure 5:
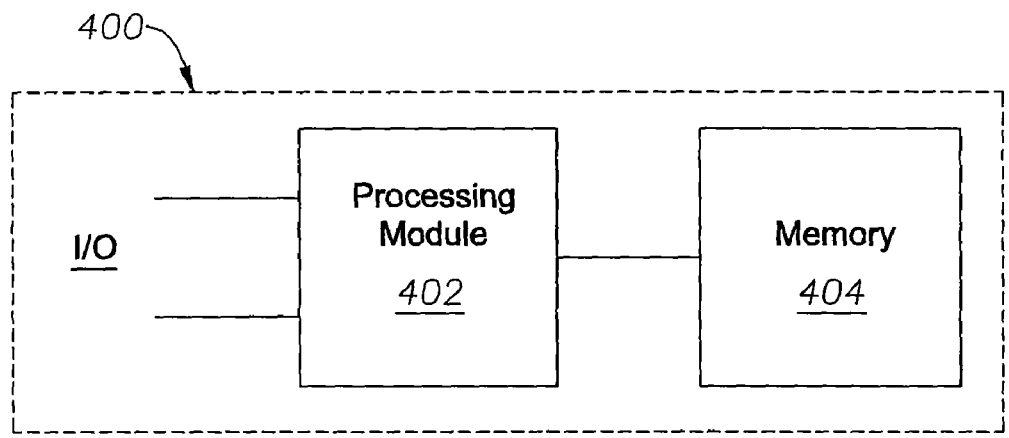
FIG. 5 is a functional block diagram of an embodiment of an apparatus for auto-titrating a laser in accordance with the present invention.

A further embodiment of the present invention can comprise an apparatus for auto-titrating a surgical laser. As shown in FIG. 5, the apparatus 400 can comprise a processing module 402 and a memory 404. Processing module 402 may be a single processing device or a plurality of processing devices. Such a processing device may be a microprocessor, microcontroller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. Memory 404 may be a single memory device, a plurality of memory devices, and/or embedded circuitry of the processing module. Memory 404 may be a read-only memory, random access memory, volatile memory, non-volatile memory, static memory, dynamic memory, flash memory, cache memory, and/or any device that stores digital information. Note that when the processing module 402 implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Further note that, the memory 404 stores, and the processing module 402 executes, hard coded and/or operational instructions corresponding to at least some of the steps and/or functions illustrated in FIGS. 1-4.

The present invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims. As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "coupled to" and/or "coupling" and/or includes direct coupling between items and/or indirect coupling between items via an intervening item (e.g., an item includes, but is not limited to, a component, an element, a circuit, and/or a module) where, for indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "operable to" indicates that an item includes one or more of power connections, input(s), output(s), etc., to perform one or more its corresponding functions and may further include inferred coupling to one or more other items. As may still further be used herein, the term "associated with", includes direct and/or indirect coupling of separate items and/or one item being embedded within another item. As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

While the present invention has been described with reference to the general area of laser ophthalmic surgery, the teachings contained herein can apply equally to any surgical system where it is desirous to control a laser subsystem.

What is claimed is:

1. A method for auto-titrating a laser, comprising:
   providing an algorithm, wherein the algorithm is operable to configure the laser based on one or more user inputs;
   providing a first user input operable to cause the algorithm to execute and fire the laser in a defined pattern; and
   providing a second user input, operable to cause the laser to stop firing and to cause the algorithm to determine one or more laser parameter values and configure the laser based on the one or more laser parameter values, wherein a final laser power value at the time the laser stops firing is an input to the algorithm and wherein the algorithm determines the one or more laser parameters based on the final laser power value.

2. The method of claim 1, further comprising the step of placing the laser in a ready mode, wherein the ready mode corresponds to an operational status for performing a surgical procedure.

3. The method of claim 1, wherein the algorithm is embodied in computer executable software instructions resident on a memory and executed by a processor.

4. The method of claim 1, wherein the laser is an ophthalmic surgical laser.

5. The method of claim 1, wherein the first and second user inputs are provided by a user actuating an actuation mechanism.

6. The method of claim 5, wherein the actuation mechanism is a footswitch.

7. The method of claim 1, wherein the defined pattern of laser firing comprises a series of laser shots, wherein the power of each successive laser shot is increased by a predefined amount.

8. The method of claim 7, wherein the final laser power value is the laser power value of the last laser shot when the laser stops firing.

9. The method of claim 1, wherein the final laser power value is the laser power value of a last laser shot when the laser stops firing.

10. The method of claim 1, wherein the one or more laser parameters comprise one or more of operating laser power, laser pulse duration, and laser pulse width.

11. The method of claim 10, wherein the operating laser power equals the final laser power value less a preset amount.

12. The method of claim 11, wherein the preset amount is 20 percent of the final laser power value.

13. The method of claim 1, wherein the second user input is provided upon the occurrence of an observed condition.

14. The method of claim 13, wherein the observed condition is a whitening of the retina indicating a laser burn.

15. The method of claim 1, wherein the algorithm is provided by selecting the algorithm from a predefined list of algorithms at a laser user interface.

16. The method of claim 1, wherein the algorithm is provided by defining a set of parameters and parameter values at a laser user interface.

17. The method of claim 1, wherein providing the algorithm comprises the step of placing the laser in a titration mode and selecting an algorithm at a laser user interface.

18. An apparatus for auto-titrating a laser, the apparatus comprising:
   a user interface, the user interface adapted to receive one or more user-inputted laser control parameters;
   a processing module; and
   a memory operably coupled to the processing module, wherein the memory includes operational instructions that cause the processing module to:
      execute an algorithm, wherein the algorithm is operable to configure the laser based on the one or more laser control parameters;
      upon receiving a first user input, fire the laser in a defined pattern;

upon receiving a second user input, stop the laser firing and determine one or more laser parameter values, and configure the laser based on the one or more laser parameter values, wherein the one or more laser parameter values are determined based on a final laser power value at the time the laser stops firing.

19. The apparatus of claim 18, wherein the operational instructions further cause the processing module to place the laser in a ready mode, wherein the ready mode corresponds to an operational status for performing a surgical procedure.

20. The apparatus of claim 18, wherein the laser is an ophthalmic surgical laser.

21. The apparatus of claim 18, wherein the first and second user inputs are provided by a user actuating an actuation mechanism.

22. The apparatus of claim 21, wherein the actuation mechanism is a footswitch.

23. The apparatus of claim 18, wherein the defined pattern of laser firing comprises a series of laser shots, wherein the power of each successive laser shot is increased by a predefined amount.

24. The apparatus of claim 23, wherein the final laser power value is a laser power value of the last laser shot when the laser stops firing.

25. The apparatus of claim 18, wherein the final laser power value is a laser power value of a last laser shot when the laser stops firing.

26. The apparatus of claim 18, wherein the one or more laser control parameters comprise one or more of operating laser power, laser pulse duration, and laser pulse width.

27. The apparatus of claim 26, wherein the operating laser power equals the final laser power value less a preset amount.

28. The apparatus of claim 27, wherein the preset amount is 20 percent of the final laser power value.

29. The apparatus of claim 18, wherein the one or more laser control parameters are selectable from a predefined list at the user interface.

* * * * *